(12) United States Patent
Heinonen et al.

(10) Patent No.: US 8,783,248 B2
(45) Date of Patent: Jul. 22, 2014

(54) INHALATION ANAESTHESIA DELIVERY SYSTEM AND METHOD

(75) Inventors: Erkki Paavo Heinonen, Helsinki (FI); Tom Jak Haggblom, Vantaa (FI); Henriikka Halinen, Helsinki (FI)

(73) Assignee: General Electric Company, Schenectady, NY (US)

( * ) Notice: Subject to any disclaimer, the term of this patent is extended or adjusted under 35 U.S.C. 154(b) by 1445 days.

(21) Appl. No.: 12/031,359

(22) Filed: Feb. 14, 2008

(65) Prior Publication Data

US 2009/0050148 A1 Feb. 26, 2009

(30) Foreign Application Priority Data

Feb. 23, 2007 (EP) ...................................... 07102935

(51) Int. Cl.
*A61M 15/00* (2006.01)
*A61M 16/00* (2006.01)
*A61B 5/08* (2006.01)

(52) U.S. Cl.
USPC ...................................... 128/203.14; 600/532

(58) Field of Classification Search
USPC ............. 128/203.12, 203.14, 203.25, 204.18, 128/204.21–204.23, 205.11; 600/532
See application file for complete search history.

(56) References Cited

U.S. PATENT DOCUMENTS

| | | | | |
|---|---|---|---|---|
| 4,423,739 | A * | 1/1984 | Passaro et al. | 600/532 |
| 5,320,093 | A * | 6/1994 | Raemer | 128/203.12 |
| 6,761,165 | B2 | 7/2004 | Strickland, Jr. | |
| 6,807,965 | B1 | 10/2004 | Hickle | |
| 2002/0017300 | A1 * | 2/2002 | Hickle et al. | 128/204.22 |
| 2005/0103338 | A1 | 5/2005 | Bunke et al. | |
| 2005/0109340 | A1 | 5/2005 | Tehrani | |
| 2006/0090757 | A1 | 5/2006 | Dittmann | |

FOREIGN PATENT DOCUMENTS

| | | |
|---|---|---|
| WO | WO 99/62403 A1 | 12/1999 |
| WO | WO04/000400 A2 | 12/2003 |
| WO | WO 2007/012197 * | 2/2007 |

* cited by examiner

*Primary Examiner* — Kristen Matter

(74) *Attorney, Agent, or Firm* — Global Patent Operation; Marc A. Vivenzio

(57) ABSTRACT

An inhalation anesthesia delivery system and method, wherein the system includes a fresh gas feeding arrangement connected to a breathing circuit, a monitor device, a control device and an interface unit. The fresh gas feeding arrangement is configured to deliver a desired concentration of gas to the breathing circuit, the desired concentration being set by using the interface unit. The monitor device is configured to monitor gas concentrations in the breathing circuit by analyzing gases flowing in the breathing circuit, and the control device is configured to control the fresh gas feeding arrangement on the basis of the data received from the monitor device to keep the desired breathing gas concentration. The control device is also configured to monitor expired inorganic gas concentration by comparing the measured expired breathing gas concentration with the set target value and changing the fresh gas delivery accordingly to meet the target value.

17 Claims, 2 Drawing Sheets

INHALATION ANAESTHESIA DELIVERY SYSTEM AND METHOD

BACKGROUND

1. Field of the Invention

The field of the invention relates to an inhalation anaesthesia delivery systems generally, and more particularly to an inhalation anaesthesia delivery system comprising a fresh gas feeding arrangement connected to a breathing circuit, a monitor device, a control device and an interface unit, whereby the fresh gas feeding arrangement and the ventilator are configured to deliver a desired concentration of gas to the breathing circuit, and to a method of operating the same.

2. Description of Prior Art

The inhalation anaesthesia delivery systems are used to maintain oxygen (O2) and carbon dioxide (CO2) exchange of the patient during anaesthesia. During inspiration oxygen enriched gas flows into the lungs where it is diffused into circulation. At the same time CO2 is diffusing from the circulation into the lungs. During expiration the oxygen depleted and CO2 enriched gas flows out from the lungs. Inspiration and expiration together form a breath. The amount of delivered gas in single breath is called tidal volume. Inspiration may be either spontaneous action of the patient or artificial when a ventilator pressurizes the lungs with fresh gas. Expiration is spontaneous in both cases and effected by lung elastic forces.

Breathing gas is often mixed with anaesthesia gases to provide The inhalation anaesthesia. These gases are nitrous oxide (N2O) or air, and volatile anaesthetics. Patient concentration determines gas exchange status (O2, CO2) and the depth of anaesthesia of the patient. Normal range for N2O is 30%-75% and for volatile agents depending on the agent from 0.7% (halothane) to 3% (sevoflurane, enflurane, isoflurane) and up to 6%-12% with desflurane. CO2 concentration is typically about 5% and O2 concentration 25%-75%. Patient concentration is the best measured as end-expiration (=end-tidal) breathing gas concentration. However, oxygen delivery is often measured with inspiration gas O2 concentration.

Anaesthesia is delivered using rebreathing circuit where expired gas is circulated after removal of carbon dioxide and adding fresh gas back to inspiration. The proportion of circulated gas increases with decreasing fresh gas flow. To save anaesthetic gases, the fresh gas flow is minimized. In low flow, minimal flow, and closed circuit anaesthesia the circulated gas conforms the majority of the new breath. During anaesthesia, oxygen delivery is fitted with patient oxygen demand. In case delivery is low compared to demand patient oxygen reservoir is emptying and vice versa. Difficulty to control the oxygen reservoirs arises in low fresh gas flows where the system time constant for the control may be measured in tens of minutes. This can be shortened with temporary major increase of the fresh gas flow. Similar increase boosts also anaesthetic agent delivery change when required, but if this is not expected, vaporizer setting needs to be compensated for the fresh gas flow change. These back-and-forth controls made manually grab the attention of the anaesthesiologist from the patient. Recent development asks for increase in safety and efficacy, which promotes automatic control loops controlling the breathing actuators in response to the measured values. Increased automation free up the human resources in operating room to concentrate on patient instead of the machine, or even take care of more patients at the same time.

The filling grade of body oxygen reservoirs can be measured with end-expiration gas oxygen concentration (EtO2), arterial blood hemoglobin oxygen saturation (SpO2), or arterial blood oxygen partial pressure (PaO2). EtO2 and SpO2 are continuous non-invasive measurements whereas the PaO2 is discrete and minimally invasive. SpO2 is insensitive on changes when the blood hemoglobin oxygen reservoir is filled and gives a delayed response only when that reservoir is already emptying. EtO2 reflects the status of all body oxygenation reservoirs including the blood hemoglobin saturation and dissolved oxygen content in blood. However, EtO2 suffers of the problem that some lung ventilation/blood perfusion mismatch conditions may disturb the connection between the measured EtO2 and body oxygen storage status. The same may occur in case the circulatory status of the patient becomes disturbed e.g. due to reduced heart pumping action. As a result of such disturbances, EtO2 measurement may overestimate the filling grade of the body oxygen reservoirs.

Expired gas control principle is not a novelty regarding anaesthesia gas delivery. Preliminary research concepts to control volatile agent vaporizers based on measured end-tidal concentrations have been presented already on 1980'ies and is today commercially available. However, known O2 control systems match either inspired gas O2 concentration US 2005/0103338A1; US2006/0090757) or patient blood measured hemoglobin (Hb) oxygen saturation (SpO2) (US 2005/0109340; U.S. Pat. No. 6,761,165) with respective setting. Disadvantage of the inspired gas control is vague correlation with patient oxygenation state, specially during instable situations where the patient O2 level is changed. Actually, O2 inspired-to-expired difference remains even at steady state whereas the difference disappears with anaesthesia gases. Controlling SpO2 involves a problem of poor sensitivity when patient oxygenation is normal, i.e. SpO2 is above 95%. On the other side, below 90% body O2 reserves are already depleted and SpO2 changes rapidly in any changes in body oxygenation state. Time constant to affect the SpO2 by changing the O2 delivery is counted at minimum tens of seconds and responding this severe situation becomes thus delayed. The problems in SpO2 rely back on S-shaped Hb saturation dissociation curve describing the saturation on the ordinate and blood O2 partial pressure on abscissa. EtO2 is closely correlated with blood O2 partial pressure and is easily measurable at the point of care with any fast responding O2 sensor capable to separate inspiration and expiration concentrations.

SUMMARY OF THE INVENTION

An embodiment of the invention provides a system by which the disadvantages of the prior art can be eliminated. This is obtained with the invention. The system of the invention is characterized in that the monitor device is configured to monitor expired inorganic gas oxygen concentration by comparing the measured expired breathing gas concentration with the set target value and changing the fresh gas delivery accordingly to meet the target value. The method of the invention is characterized in that expired inorganic gas concentration is monitored by comparing the measured expired breathing gas concentration with the set target value and the fresh gas delivery is changed accordingly to meet the target value.

An advantage of the invention is in its simplicity and ability to produce reliable results, i.e. end tidal oxygen (EtO2) is closely correlated with blood O2 partial pressure and is easily measurable at the point of care with any fast responding O2 sensor capable to separate inspiration and expiration concentrations.

As described above in this invention expired gas mixture concentration is controlled automatically with a control system comparing the measured end-tidal concentration with the target value and changing the fresh gas composition accordingly to meet the target. Expired gas mixture is measured for O2, N2O, CO2, and AA concentrations. User selects the gas delivered with O2 from the two of N2O and air and the end-tidal target concentrations for O2 and anaesthetic agent. Control device determines from the differences between the measured and target values set the demand to change fresh gas composition. When the EtO2 concentration change is required, fresh gas flow rate is increased and the concentration is adjusted respectively to meet the demanded change. At this time, if anaesthetic concentration change is not expected, vaporized setting is dialled down. When the measured O2 concentration approaches the target, fresh gas flow is decreased to close the circuit for savings in anaesthetics, and vaporizer setting is increased to compensate for this. Respectively, change in anaesthetic agent (AA) concentration is accompanied with increased fresh gas flow to boost the AA change while controlling the delivered fresh gas mixture to preserve the end-tidal O2 concentration. In some cases, user may want to have also control over the speed of concentration change. For this purpose, a user control for maximum fresh gas flow may be provided.

To safeguard the control delivery system against the potential disturbances on connection between EtO2 and body oxygen reservoir filling grade, the control system is backed up with SpO2. For this purpose, user gives the minimum SpO2 the controller allows for. Decreasing below this minimum level oxygen delivery is automatically increased despite of the matching of target and measured end-tidal oxygen concentrations. This oxygen delivery increase may be effected by automatically increasing the EtO2 target value.

To use this invention, the operator selects the gas to be mixed with O2, and gas concentrations. Because the fresh gas is mixture of O2, secondary gas (N2O, N2 or xenon), and volatile agent, target Et concentrations may be given to any two of these gases. Advantageously the given target concentrations are end-tidal values for oxygen and volatile agent the secondary gas conforming the rest. Given also the secondary gas, the controller adjusts O2 flow, secondary gas flow, and vaporizer setting to meet the target values. The flows are adjusted within the limits of total fresh gas flow that may also be given to limit the rate of change in gas compositions, that may be used to titrate the correct end-tidal settings. When changing the secondary gas from one to another, the controller needs to control the concentrations of all three gases to replace the previous secondary gas with the new one from the breathing circuit. Finally, when the measured end-tidal values match with the target values, fresh gas flow is gradually reduced to minimize the gas, especially volatile agent, consumption. For full performance of the oxygen control, the user gives also the minimum allowed SpO2 value.

BRIEF DESCRIPTION OF THE DRAWINGS

In the following description, embodiments of the invention will be described in greater detail by means of examples shown in the attached drawings, in which.

DETAILED DESCRIPTION

Figure 1:
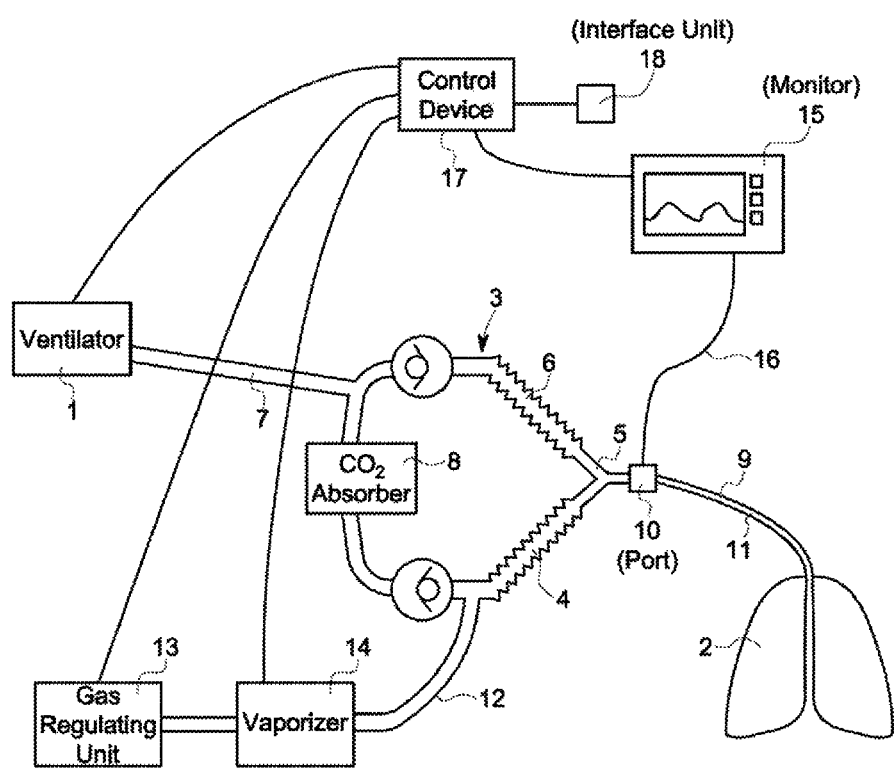
FIG. 1 shows schematically an operational environment of the system according to an embodiment of the invention.

FIG. 1 shows the anaesthesia environment the method may be applied in connection with the invention. Ventilator 1 fills patient lungs 2 during inspiration by pressurizing the breathing circuit 3. Breathing circuit comprises of inspiration limb 4, Y-piece 5, expiration limb 6, ventilator limb 7, CO2 absorber 8, and patient limb 9. Inspiration and expiration limbs include unidirectional valve to direct the inspiration and expiration gas flow to respective limbs. Patient limb includes gas monitor sampling port 10 and intubation tube 11 connecting the patient with the breathing circuit. In operation, ventilator receives the expired gas from the patient during expiration and stores the gas for the next inspiration. At inspiration the gas is guided through CO2 absorber, where the CO2 is removed, to inspiration limb and further to patient lungs. Breathing gas is brought into the breathing circuit from fresh gas line 12. The breathing gas is a mixture of O2, N2O or N2 (air) from gas regulating unit 13 and volatile agents vaporized into this gas stream in the vaporizer 14.

Alternatively patient may be breathing spontaneously. In spontaneous breathing the ventilator comprises reservoir collecting the exhalation gas and therefrom patient breathing action receives inspiration gas.

Monitor device 15, i.e. gas monitor may be of a side-stream type drawing a sample gas stream from the sampling port 10 through sampling line 16 for analysis with the sensors within the monitor. Alternatively the monitor device may be of mainstream type where the gas analysis sensors are located directly at the patient limb instead of the sampling port.

Monitor device 15 is further electrically connected to control device 17, which is further connected to the actuators (gas regulating unit 13, and/or vaporizer 14) closing the control loop. This controller compares the measured values with the user set target and tunes the actuators to match the measured values with the setting. The user can set the target by using an interface unit 18.

Figure 2:
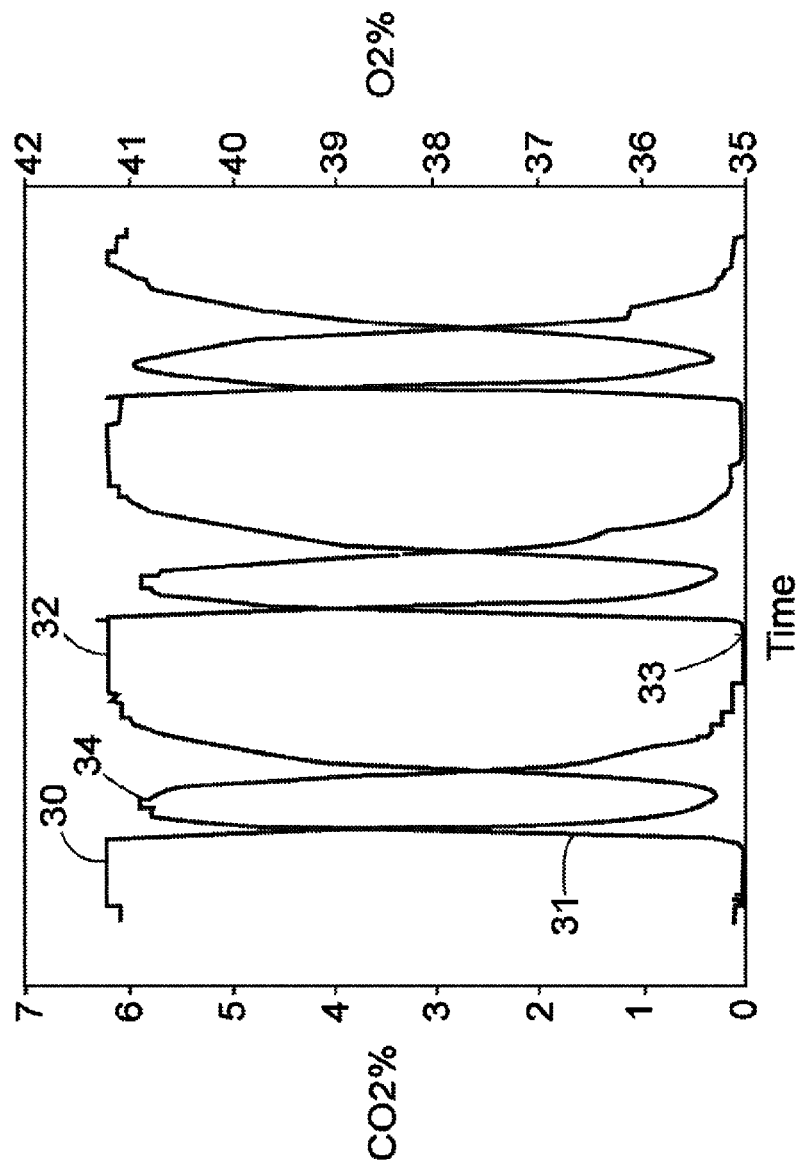
FIG. 2 shows CO2 and O2 concentration waveforms in patient breathing.

FIG. 2 presents CO2 30 and oxygen 31 concentration waveforms with reference to time on abscissa. End-tidal value, the best non-invasive representative available for alveolar and further blood gas partial pressure, is advantageously determined from CO2 waveform, because it is more uniform in varying clinical conditions. The end-tidal value for CO2 32 is determined as the maximum value during the breath cycle. At steady state, as shown in FIG. 2, end-tidal oxygen 33 is the minimum of the O2 waveform during the breath cycle. However, during transients when inspired O2 concentration 34 is reduced, the end-tidal oxygen may be the oxygen waveform maximum. To better handle these transient situations, oxygen end-tidal value is advantageously determined as the waveform value at the time of recording the end-tidal CO2.

To control the end-tidal gas mixture, the control device needs to increase the fresh gas flow rate as a response to differences in end-tidal to target gas concentration. This comparison takes into consideration the differences between:

Measured Et O2−target Et O2;

Measured Et AA−target Et AA;

3a) N2O selected as a secondary gas: N2 concentration target is zero. Direct N2 concentration measurement is often not available, thus that needs to be calculated using the other gas mixture components as EtN2=100−EtO2−EtCO2−EtN2O−EtAA.

3b) N2 (air) selected as secondary gas: N2O concentration target is zero.

Fresh gas flow demand is determined for each of these differences. This determination advantageously increases fresh gas flow demand as a response to increased difference to boost the concentration change speed. Respectively decreased difference would end up to decreased flow demand to save the gases. Such response can be achieved e.g. with linear relationship equation between the flow demand and difference. The final target fresh gas flow value is determined from the comparison results 1-3. As an example, the target fresh gas flow can be the largest of the flows 1-3. Providing possibility to limit fresh gas flow maximum, user may control the concentration change speed, which is useful in titrating the optimum fresh gas mixture. Respectively, minimum fresh gas flow can be given to assure minimum breathing circuit clearance from patient- or system derived gas compounds that may accumulate in closed circuit.

Now, using the fresh gas flow value and difference 1), fresh gas oxygen concentration is calculated. In this context the fresh gas flow value may be either the measured or target value. Respectively, for anaesthesia gas a new fresh gas AA concentration is calculated from difference 2) and the flow.

Finally, using the fresh gas flow and fresh gas oxygen concentration, the target settings for the fresh gas oxygen flow and secondary gas flow is calculated. This final calculation is straightforward when having N2O as secondary gas, but with air the mixture content of 21% O2 has to be taken into consideration in this final flow calculation. The calculated flow values are then sent to the gas mixer and vaporizer for new settings. Alternatively, if the gas mixer operates with the principle of total flow & O2% control, then these are used for respective target settings instead of the flows.

The embodiment of the invention described above is by no means intended to restrict the invention but the invention can be varied completely freely within the scope of the claims. Therefore it is obvious that the system or its details do not necessary have to be exactly the same as shown in the figures but other solutions are possible, too.

What is claimed is:

1. An inhalation anesthesia delivery system, comprising:
a fresh gas feeding arrangement connected to a breathing circuit;
a monitor device;
a control device; and
an interface unit;
wherein the interface unit is configured to be used to input at least two set target gas concentration values including at least a set target end tidal oxygen (EtO2) concentration value and a set target end tidal volatile anesthetic agent concentration value;
the fresh gas feeding arrangement is configured to deliver a desired concentration of gas including at least a desired concentration of oxygen to the breathing circuit;
the monitor device is configured to monitor and measure at least two expired gas concentration values including an expired end tidal oxygen (EtO2) concentration value and an expired end tidal volatile anesthetic agent concentration value by analyzing expiration gases in the breathing circuit; the control device is configured to receive the at least two set target gas concentration values including the target end tidal oxygen (EtO2) concentration value and the set target end tidal volatile anesthetic agent concentration value from the interface unit, receive the at least two expired gas concentration values from the monitor device, and to provide the desired concentration of gas including at least the desired concentration of oxygen (O2) to the breathing circuit via the fresh gas feeding arrangement; and
the control device is further configured to control the at least two expired gas concentration values by comparing at least the measured expired end tidal oxygen (EtO2) concentration value with the set target end tidal oxygen (EtO2) concentration value and the measured expired end tidal volatile anesthetic agent concentration value with the set target end tidal volatile anesthetic agent concentration value, and changing the desired concentration of gas including the desired concentration of oxygen delivered to the breathing circuit accordingly to meet the at least two set target gas concentration values;
wherein, when the measured at least two expired end tidal concentration values are about equal to the at least two set target gas concentration values, the control device is further configured to reduce fresh gas flow to minimize consumption of the volatile anesthetic agent.

2. The inhalation anesthesia delivery system of claim 1, wherein the monitor device is configured to further measure expired gas concentrations for at least one of N2O, and CO2.

3. The inhalation anesthesia delivery system of claim 1, wherein the monitor device is configured to further measure expired gas concentrations for N2O or N2, and the control device is configured to compare the corresponding measured values to corresponding set target values.

4. The inhalation anesthesia delivery system of claim 1, wherein the control device is also configured to monitor an SpO2 value and compare said value with an allowed minimum SpO2 value set by using the interface unit.

5. The inhalation anesthesia delivery system of claim 4, wherein the control device is configured to receive set maximum and minimum values for fresh gas flow.

6. The inhalation anesthesia delivery system of claim 1, wherein the control device is configured to monitor differences between the at least two end-tidal concentration values and the at least two set target gas concentration values.

7. The inhalation anesthesia delivery system of claim 1, wherein the delivery system further comprises a ventilator.

8. The inhalation anesthesia delivery system of claim 1, wherein the changing the fresh gas delivery is carried out by changing composition or/and flow rate.

9. A method of operating an inhalation anesthesia delivery system, the method comprising:
inputting at least two set target gas concentration values including at least a set target end tidal oxygen (EtO2) concentration value and a set target end tidal volatile anesthetic agent concentration value into the system via an interface unit;
delivering via a fresh gas feeding arrangement a desired concentration of gas including at least a desired concentration of oxygen to a breathing circuit;
monitoring and measuring with a monitor device at least two expired gas concentration values including an expired end tidal oxygen (EtO2) concentration value and an expired end tidal volatile anesthetic agent concentration value by analyzing expiration gases flowing in the breathing circuit;
receiving via a control device the at least two set target gas concentration values from the interface unit, and the at least two expired gas concentration values from the monitor device;
providing via the control device the desired concentration of gas including at least the desired concentration of oxygen to the breathing circuit via the fresh gas feeding arrangement;
controlling with the control device the at least two expired gas concentration values by comparing the expired end tidal oxygen (EtO2) concentration value with the set target end tidal oxygen concentration (EtO2) value and the measured expired end tidal volatile anesthetic agent concentration value with the set target end tidal volatile anesthetic agent concentration value;
changing the desired concentration of fresh gas delivery to the breathing circuit including the desired concentration of oxygen (O2) delivery accordingly to meet the at least two set target gas concentration values; and reducing fresh gas flow to minimize consumption of the volatile anesthetic agent when the measured at least two end tidal concentration values are about equal to the at least two set target gas concentration values.

10. The method of claim 9, further comprising:
measuring expired breathing gas concentrations for at least one of N2O, and CO2.

11. The method of claim 10, wherein the inputting step includes:
inputting at least one set target inorganic gas concentration value for any of N2O or N2.

12. The method of claim 11, wherein the controlling step includes:
comparing the set target concentration values for N2O or N2 with corresponding measured expired gas concentration values for N2O or N2.

13. The method of claim 9, further comprising:
monitoring an SpO2 concentration value; and
comparing said monitored SpO2 value with an allowed minimum SpO2 value.

14. The method of claim 9, wherein differences between the measured at least two end-tidal concentration values and the at least two set target gas concentration values are monitored.

15. The method of claim 14, wherein maximum and minimum values for fresh gas flow are set.

16. The method of claim 9, wherein the delivery system further comprises a ventilator.

17. The method of claim 9, wherein the changing the fresh gas delivery is carried out by changing composition or/and flow rate.

* * * * *